United States Patent
Zhou

(10) Patent No.: US 9,926,203 B2
(45) Date of Patent: Mar. 27, 2018

(54) METHOD OF MAKING 2,2,4,4-TETRASILYLPENTASILANE

(71) Applicant: Dow Corning Corporation, Midland, MI (US)

(72) Inventor: Xiaobing Zhou, Midland, MI (US)

(73) Assignee: DOW CORNING CORPORTION, Midland, MI (US)

( * ) Notice: Subject to any disclaimer, the term of this patent is extended or adjusted under 35 U.S.C. 154(b) by 48 days.

(21) Appl. No.: 14/915,404

(22) PCT Filed: Sep. 3, 2014

(86) PCT No.: PCT/US2014/053774
§ 371 (c)(1),
(2) Date: Feb. 29, 2016

(87) PCT Pub. No.: WO2015/034855
PCT Pub. Date: Mar. 12, 2015

(65) Prior Publication Data
US 2016/0207784 A1    Jul. 21, 2016

Related U.S. Application Data

(60) Provisional application No. 61/874,064, filed on Sep. 5, 2013.

(51) Int. Cl.
| | |
|---|---|
| *C01B 33/04* | (2006.01) |
| *C07F 7/02* | (2006.01) |
| *C23C 16/24* | (2006.01) |
| *H01L 21/02* | (2006.01) |
| *C23C 18/12* | (2006.01) |
| *C23C 16/50* | (2006.01) |

(52) U.S. Cl.
CPC .............. *C01B 33/04* (2013.01); *C07F 7/025* (2013.01); *C23C 16/24* (2013.01); *C23C 16/50* (2013.01); *C23C 18/1212* (2013.01); *H01L 21/0214* (2013.01); *H01L 21/0217* (2013.01); *H01L 21/0262* (2013.01); *H01L 21/02164* (2013.01); *H01L 21/02211* (2013.01); *H01L 21/02274* (2013.01); *H01L 21/02282* (2013.01); *H01L 21/02529* (2013.01); *H01L 21/02532* (2013.01); *H01L 21/02628* (2013.01); *H01L 21/02639* (2013.01)

(58) Field of Classification Search
CPC ..... C01B 33/04; C01B 33/043; C01B 33/046; C01B 33/00
USPC .................................................. 423/347, 324
See application file for complete search history.

(56) References Cited

U.S. PATENT DOCUMENTS

| | | |
|---|---|---|
| 5,942,637 A | 8/1999 | Boudjouk et al. |
| 8,147,789 B2 | 4/2012 | Cannady et al. |
| 8,163,261 B2 | 4/2012 | Hazeltine |
| 8,535,760 B2 | 9/2013 | Hurley et al. |
| 8,969,610 B2 | 3/2015 | Wieber et al. |
| 8,975,429 B2 | 3/2015 | Elangovan et al. |

OTHER PUBLICATIONS

Grev, Roger S., et al.; In search of triplet silylenes, Journal of the American Chemical Society, vol. 113, No. 15, Jul. 1, 1991 (Jul. 1, 1991), pp. 5638-5643.

K.H. Chung, et al, The High Growth Rate of Epitaxial Silicon-Carbon Alloys by Using Chemical Vapour Deposition and Neopentasilane, Semiconductor Science and Technology, 2007, vol. 22, S158-S160.

T. Shimoda, et al, Solution-Processed Silicon Films and Transistors, Nature, vol. 440, Apr. 2006, 783-786.

*Primary Examiner* — Edward Johnson
(74) *Attorney, Agent, or Firm* — Matthew T. Fewkes

(57) ABSTRACT

A compound that is 2,2,4,4-tetrasilylpentasilane, chemical compositions comprising same, methods of making and purifying 2,2,4,4-tetrasilylpentasilane, the purified 2,2,4,4-tetrasilylpentasilane prepared thereby, and methods of forming silicon-containing materials using 2,2,4,4-tetrasilylpentasilane as a precursor.

12 Claims, No Drawings

METHOD OF MAKING 2,2,4,4-TETRASILYLPENTASILANE

CROSS REFERENCE TO RELATED APPLICATIONS

This application is a U.S. national stage filing under 35 U.S.C. § 371 of PCT Application No. PCT/US14/53774 filed on Sep. 3, 2014, currently pending, which claims the benefit of U.S. Provisional Patent Application No. 61/874,064 filed Sep. 5, 2013, under 35 U.S.C. § 119 (e). PCT Application No. PCT/US14/53774 and U.S. Provisional Patent Application No. 61/874,064 are hereby incorporated by reference.

This invention generally relates to 2,2,4,4-tetrasilylpentasilane, chemical compositions comprising same, methods of making and purifying 2,2,4,4-tetrasilylpentasilane, the purified 2,2,4,4-tetrasilylpentasilane prepared thereby, and methods of forming silicon-containing materials using 2,2,4,4-tetrasilylpentasilane as a precursor.

A silicon-containing material (e.g., film) may be used as a semiconductor, an insulating layer or a sacrificial layer in the manufacture of electronic circuitry for electronic or photovoltaic devices. Silicon-containing films suitable for such use may be prepared from one or more silicon-containing precursors by a film-forming deposition method.

The silicon-containing precursor may be a silazane, siloxane, silane, or other silicon-containing molecule. The silane-type precursor may be an (alkyl)aminosilane, a halosilane, an organosilane, or a hydridosilane. The hydridosilane may be monosilane, disilane, or a higher order hydridosilane. Volatile precursors containing from 1 to 5 silicon atoms (e.g., ($Si_1$-$Si_5$) precursors) may be used in vapor-based material (e.g., film) forming methods wherein reaction by-products are removed from the formed material (e.g., film) via evaporation or gas sweeping. Nonvolatile precursors containing 80 silicon atoms (e.g., $Si_{80}$ precursors) may be used in solution-based material (e.g., film) forming methods wherein the solvent in which the nonvolatile precursor is dissolved must be removed from the formed material via evaporation or gas sweeping without removal of the nonvolatile precursor.

Some methods of synthesizing silicon-containing precursors and films are known. For example, DE2139155 A1 by Plichta P. mentions, among other things, a method of synthesizing higher silanes and higher germanes by pyrolysis in a column packed with glass wool-silica gel-platinum (5%) catalyst and fractionation of the resulting mixture of products. Reactants used in the method are trisilane, norma/-tetrasilane, and norma/-pentasilane.

U.S. Pat. No. 5,700,400 to Ikai K., et al. mentions, among other things, a method for producing a semiconducting material by subjecting a hydrosilane monomer to dehydrogenative condensation followed by thermal decomposition. The hydrosilane monomer may be a hydromonosilane, a hydrodisilane, or a hydrotrisilane. The dehydrogenative condensation is conducted in the presence of a catalyst that contains at least one metal or metal compound of "Groups 3B, 4B and 8 of the Periodic Table."

U.S. Pat. No. 8,147,789 B2 to Cannady, J. P. and Zhou, X., and assigned to Dow Corning Corporation, describes a composition comprising at least 93% (w/w) of neopentasilane; and a method of preparing neopentasilane.

US 2012/0291665 A1 by Wieber S., et al. mentions, among other things, a method for oligomerizing hydridosilanes in the absence of a catalyst. The method employs a composition comprising substantially at least one non-cyclic hydridosilane having a maximum of 20 silicon atoms as the hydridosilane is thermally converted at temperatures below 235° C. in the absence of a catalyst. The hydridosilane may be, e.g., neopentasilane.

The present inventor has discovered or recognized technical problems with using commercial silicon-containing precursors to prepare silicon-containing materials (e.g., films) for use in manufacture of electronic or photovoltaic devices. As geometries of electronic and photovoltaic circuitry become finer and smaller, silicon-containing films prepared from commercial silicon-containing precursors are found to have inadequate performance for such circuitry. For example, in newer electronic circuitry aspect ratios of trenches between line features are being increased. Higher aspect ratios mean trenches become taller and distances or spacings between lines become shorter. Such narrower trenches or denser line packing improve electronic performance. Silicon-containing films made from commercial precursors, however, are found to have thermal budgets that are too high for use in low temperature deposition methods and/or have inadequate conformality for covering interior surfaces of the finer trenches during manufacture of the finer and smaller electronic or photovoltaic circuitry.

Further, the present inventor has discovered or recognized technical problems with prior methods of synthesizing higher order hydridosilanes. Despite decades of research, however, synthesis of higher order hydridosilanes has been difficult. Some higher order silanes have been made through hydrolysis of metal silicides or energetic (e.g., thermal) treatment of monosilane or disilane. But these methods are non-selective and unproductive in that they undesirably have low yields and produce mixtures of higher order silanes. The lack of a broad toolbox of different silicon-containing precursors and the absence of commercially feasible methods of selectively synthesizing same have thwarted discovery of improved silicon-containing films.

BRIEF SUMMARY OF THE INVENTION

The present inventor has discovered a new silicon-containing precursor and a method of selectively synthesizing same. The silicon-containing precursor may be used in a material forming deposition method to prepare silicon-containing materials having improved performance for use in manufacture of electronic or photovoltaic devices. The silicon-containing precursor generally is a silane, particularly a hydridosilane, more particularly a higher order hydridosilane, still more particularly a nonasilane, even more particularly a nonasilane structural isomer, and yet even more particularly, 2,2,4,4-tetrasilylpentasilane. Embodiments of the invention include:

A compound that is 2,2,4,4-tetrasilylpentasilane.

A chemical composition comprising 2,2,4,4-tetrasilylpentasilane and one or more additional ingredients that differ from 2,2,4,4-tetrasilylpentasilane.

A method of making 2,2,4,4-tetrasilylpentasilane, the method comprising contacting 2,2-disilyltrisilane with a condensation reaction catalyst under condensation reaction conditions so as to synthesize the 2,2,4,4-tetrasilylpentasilane and make a product composition comprising the 2,2,4,4-tetrasilylpentasilane.

A method of purifying 2,2,4,4-tetrasilylpentasilane, the 2,2,4,4-tetrasilylpentasilane before purification being in a mixture comprising 2,2,4,4-tetrasilylpentasilane, monosilane, and 2,2-disilyltrisilane, the method comprising separating the monosilane and 2,2-disilyltrisilane from the 2,2,4,4-tetrasilylpentasilane to give a remainder comprising 2,2,4,4-tetrasilylpentasilane and lacking the separated monosilane and 2,2-disilyltrisilane, wherein concentration of the 2,2,4,4-tetrasilylpentasilane in the remainder is greater than concentration of the 2,2,4,4-tetrasilylpentasilane in the mixture.

A method of forming a silicon-containing material on and in contact with a surface of a first substrate or on and in contact with a seed layer disposed on a second substrate, the method comprises contacting an exposed surface of a first substrate lacking a seed layer or contacting a seed layer disposed on a surface of a second substrate, to vapor of a precursor composition comprising 2,2,4,4-tetrasilylpentasilane, wherein the contacting comprises a material deposition method and forms a silicon-containing material on and in contact with the exposed surface of the first substrate or on and in contact with the seed layer disposed on the surface of the second substrate.

The 2,2,4,4-tetrasilylpentasilane, chemical composition, and product composition independently are useful as, among other uses, a silicon-containing deposition precursor for forming silicon-containing materials, including crystalline silicon and other silicon-containing materials. The method of making the 2,2,4,4-tetrasilylpentasilane is useful for selectively synthesizing 2,2,4,4-tetrasilylpentasilane while not making, or making comparatively minor amounts, of other nonasilane structural isomers. The selectivity of the method is such that prior to purification the product composition lacks any other nonasilane structural isomer, alternatively has at most a total of from >0 to 9 area % (GC) of nonasilane structural isomers other than the 2,2,4,4-tetrasilylpentasilane. The method of purifying is useful for preparing a purified form (remainder portion), alternatively a purified and distilled form (distillate), of the 2,2,4,4-tetrasilylpentasilane. The method of forming is useful for forming silicon-containing materials. The silicon-containing materials are useful in the manufacture of electronic and photovoltaic devices or circuitry, including finer and smaller circuitry for or in electronic and photovoltaic devices. The invention may have additional uses, including those unrelated to electronic and photovoltaic applications.

DETAILED DESCRIPTION OF THE INVENTION

The Brief Summary and Abstract are incorporated here by reference. The invention includes, but is not limited to, the embodiments, uses and advantages summarized above. These embodiments include the 2,2,4,4-tetrasilylpentasilane, chemical compositions comprising same, methods of making and purifying 2,2,4,4-tetrasilylpentasilane, the purified 2,2,4,4-tetrasilylpentasilane prepared thereby, and method of forming silicon-containing materials using 2,2,4,4-tetrasilylpentasilane as a silicon-containing material forming precursor. The formed silicon-containing material may be a silicon-containing film and the method of forming may be a method of forming same. The invention includes more embodiments, which are described below.

The invention has technical and non-technical advantages. It is convenient to illustrate some of the advantages vis-à-vis forming silicon-containing materials that are silicon-containing films, but the invention and advantages are not limited to forming such films. For example, the 2,2,4,4-tetrasilylpentasilane may be used as a silicon-containing precursor in silicon-containing material deposition methods wherein the method requires the precursor to be volatile, as well as in silicon-containing material deposition methods wherein the method requires the precursor to be nonvolatile.

Also, the method of making the 2,2,4,4-tetrasilylpentasilane is a selective synthesis in that it produces few, if any, other nonasilane structural isomers, or it produces few, if any, other nonasilane structural isomers and few, if any, other higher order silanes besides nonasilanes. In such embodiments the method of making may be thought of as formally coupling a 2,2-disilyltrisilan-1-yl radical with a 2-silyltrisilan-2-yl radical to yield the 2,2,4,4-tetrasilylpentasilane, wherein the method may avoid forming oligomers of 2,2-disilyltrisilane. We believe that compared to monosilane, disilane, or 2,2-disilyltrisilane, the 2,2,4,4-tetrasilylpentasilane may provide a silicon-containing film having a thermal budget that allows the 2,2,4,4-tetrasilylpentasilane to be used in lower temperature deposition methods, e.g., methods conducted at 400° C. for vapor deposition of materials (e.g., films) of crystalline silicon, although higher temperatures may be used for the deposition method if desired. Lower temperature deposition methods employ a temperature that is lower than that used in benchmark film deposition. For example disilane is a benchmark precursor used to deposit a film of polycrystalline silicon at 600° C., and thus the lower temperature deposition methods employ temperatures less than 600° C., e.g., from 200° to <600° C., alternatively from 300° to <600° C., alternatively from 200° to <500° C. Alternatively or additionally, the silicon-containing film that may be produced using 2,2,4,4-tetrasilylpentasilane as a silicon-containing precursor is expected to have adequate conformality for covering interior surfaces of the finer trenches during manufacture of the smaller electronic or photovoltaic circuitry. Certain aspects of this invention may independently solve additional problems and/or have other advantages.

Abbreviations: area % (GC) is area percent determined by gas chromatography; ALD is atomic layer deposition; ALCVD is atomic layer chemical vapor deposition; APCVD is atmospheric pressure chemical vapor deposition; CVD is chemical vapor deposition; CCVD is combustion chemical vapor deposition; ° C. is degrees Celsius; DSC is differential scanning calorimetry; Ex. is Example; GC-MS is Gas Chromatograph-Mass Spectrometry; g is gram; HMBC is H—Si heteronuclear multiple bond correlation; HSQC is H—Si heteronuclear single quantum coherence; HWCVD is hot wire chemical vapor deposition; HPCVD is hybrid physical chemical vapor deposition; IUPAC is International Union of Pure and Applied Chemistry; kPa is kilopascals; LPCVD is low pressure chemical vapor deposition; μm is micron; mm is millimeter; nm is nanometer; NMR is nuclear magnetic resonance; ppm is parts per million; PICVD is photo-initiated chemical vapor deposition; PVD is physical vapor deposition; PECVD is plasma enhanced chemical vapor deposition; RTCVD is rapid thermal chemical vapor deposition; SOD is spin-on deposition; TGA is thermogravimetric analysis; UHVCVD is ultrahigh vacuum chemical vapor deposition; VPE is vapor phase epitaxy; wt % is weight percent; w/w is weight/weight.

As used herein the term "chemical composition" means matter that may be defined by an empirical formula of its constituent elements.

The terms "comprises" and "comprised of" are synonymous and are open ended.

The term "condensation reaction catalyst" means a substance that is effective for enhancing self-condensation of 2,2-disilyltrisilane compared to a self-condensation reaction lacking the substance. The term "enhance" in this context includes reducing time to onset of reaction, lowering temperature at which reaction initiates, increasing reaction rate, or a combination of any two or more thereof.

The term "condensation reaction conditions" means a combination of circumstances that facilitate self-condensation of 2,2-disilyltrisilane. Examples of such circumstances are reaction temperature, reaction pressure, reaction period (length of time), gas atmosphere, and order of addition of components of the reaction mixture.

The term "hydridosilane" means a saturated silicon hydride molecule consisting of Si and H atoms. Examples include monosilane ($SiH_4$), disilane ($H_3SiSiH_3$), and higher order hydridosilanes.

The term "higher order hydridosilane" is a saturated silicon hydride molecule that consists of hydrogen atoms and at least 3 Si atoms. For present purposes, the higher order hydridosilane is described by the formula $Si_nH_{(2n+2)}$ for straight and branched chains or the formula $Si_nH_{2n}$ for cyclic chains, wherein each n independently is an integer of 3 or greater.

The term "lack" means a complete absence of, e.g., 0 wt % or 0 area % (GC).

The term "material-forming deposition" is a process of generating, on a specific place, condensed matter that is not restricted in dimension. The term "film-forming deposition" is a process of generating, on a specific place, condensed matter restricted in one dimension.

Neopentasilane is a common name for 2,2-disilyltrisilane, which has the formula $H_3Si$—$Si(SiH_3)_2$—$SiH_3$ or, simply, $Si(SiH_3)_4$.

The term "nonasilane" means a saturated silicon hydride molecule having nine silicon atoms and the remaining atoms are hydrogen atoms. Typically, nonasilane has either one of the following molecular formulas: $Si_9H_{20}$ for straight or branched chain molecules or $Si_9H_{18}$ for monocyclic molecules, alternatively $Si_9H_{20}$, alternatively $Si_9H_{18}$.

The term "product composition" means a chemical composition having at least one ingredient, wherein the at least one ingredient is produced by a method of this invention.

The term "purify" means increase concentration of a desired ingredient (up to 100 wt %), decrease concentration of one or more undesired ingredients (down to 0 wt %), or both.

The term "remainder" means a portion which is left behind, e.g., a pot residue after a distillation.

The term "selective synthesis" means preferential making of a molecule over other made molecules. In determining selectivity of a synthesis, any impurities in reactants and any products made from those impurities in the synthesis are not considered.

The term "separate" means to cause to physically be apart, and thus no longer in direct touching.

The term "silicon-containing material" means condensed matter that is not restricted in dimension, wherein the condensed matter comprises atoms of element 14 of the Periodic Table of the Elements, published 2011 by the IUPAC. The silicon-containing material may consist essentially of elemental silicon (i.e., lacks other elements except for dopants or impurities), or may comprise molecules containing Si atoms and at least one atom selected from O, C, or N. The term "silicon-containing film" means silicon-containing material that is restricted in one dimension. The restricted dimension may be characterized as "thickness" and as the dimension that, all other things being equal, increases with increasing length of time of silicon-containing material deposition.

The term "silicon-containing precursor" means a substance or molecule containing atoms of element 14 and useful for forming the silicon-containing material (e.g., film) in a material (e.g., film)-forming deposition method.

The term "structural isomer" means a molecule having, relative to a comparative molecule, the same atomic composition (same molecular formula), but different line formula (bonding arrangement) or different stereochemical formula, and thus different physical or chemical properties (e.g., boiling point or rotation of plane polarized light).

The term "substrate" means a physical support having at least one surface upon which a layer of a material may be hosted. The substrate may be composed of any material suitable for supporting a silicon-containing material (e.g., film). The material may be homogeneous or heterogeneous (e.g., a composite material or structure). The substrate or a surface thereof may be continuous or discontinuous.

As used herein, "may" confers a choice, not an imperative. "Optionally" means is absent, alternatively is present. "Contacting" means bringing into physical contact. "Operative contact" comprises functionally effective touching, e.g., as for modifying, coating, adhering, sealing, or filling. The operative contact may be direct physical touching, alternatively indirect touching. All U.S. patent application publications and patents referenced herein, or a portion thereof if only the portion is referenced, are hereby incorporated herein by reference to the extent that incorporated subject matter does not conflict with the present description, which would control in any such conflict. All states of matter are determined at 25° C. and 101.3 kPa unless indicated otherwise. All % are by weight unless otherwise noted. All wt % values are, unless otherwise noted, based on total weight of all ingredients used to synthesize or make the composition, which adds up to 100 wt %. Any Markush group comprising a genus and subgenus therein includes the subgenus in the genus, e.g., in "R is hydrocarbyl or alkenyl," R may be alkenyl, alternatively R may be hydrocarbyl, which includes, among other subgenuses, alkenyl.

The compound that is 2,2,4,4-tetrasilylpentasilane has the molecular formula $Si_9H_{20}$ and the structural formula $H_3Si$—$Si(SiH_3)_2$—$SiH_2$—$Si(SiH_3)_2$—$SiH_3$. The compound that is 2,2,4,4-tetrasilylpentasilane may be a natural abundance isotope form, alternatively an isotopically-enriched form, alternatively a mixture thereof. The isotopically-enriched forms of 2,2,4,4-tetrasilylpentasilane include forms that contain a greater-than-natural-abundance amount of deuterium, tritium, $^{29}Si$, $^{30}Si$, $^{32}Si$, or a combination of any two or more thereof. In addition to the uses of 2,2,4,4-tetrasilylpentasilane described herein, isotopically enriched forms of 2,2,4,4-tetrasilylpentasilane may be useful in applications wherein detection of the enriched 2,2,4,4-tetrasilylpentasilane or an enriched silicon-containing material (e.g., film) made therefrom would be helpful. Examples of such applications are medical research and anti-counterfeiting applications. For example, the 2,2,4,4-tetrasilylpentasilane may consist of 99 wt % of a natural abundance isotope form of 2,2,4,4-tetrasilylpentasilane and 1 wt % of an isotopically enriched 2,2,4,4-tetrasilylpentasilane. The compound that is 2,2,4,4-tetrasilylpentasilane and the chemical composition comprising same may be stored under an anhydrous condition (i.e., lacking water), under an inert atmosphere, or, typically, both. The inert atmosphere may be a gas of molecular nitrogen, helium, argon, or a mixture of any two or more thereof.

The chemical composition comprises the 2,2,4,4-tetrasilylpentasilane. The chemical composition may contain one or more additional ingredients that differ from 2,2,4,4-tetrasilylpentasilane. That is, the one or more additional ingredients are not the 2,2,4,4-tetrasilylpentasilane. The additional ingredient(s) may be in admixture with the 2,2, 4,4-tetrasilylpentasilane. Alternatively, at least one additional ingredient may be in direct physical contact with, but substantially not in admixture with, the 2,2,4,4-tetrasilylpentasilane. The additional ingredient(s) may be any substance suitable for use with the 2,2,4,4-tetrasilylpentasilane other than that of the 2,2,4,4-tetrasilylpentasilane. Such use may comprise synthesis, purification, storage, transportation, and/or reaction of the 2,2,4,4-tetrasilylpentasilane. The use may comprise reaction of the 2,2,4,4-tetrasilylpentasilane. The reaction of the 2,2,4,4-tetrasilylpentasilane may comprise the method of forming a silicon-containing material (e.g., film).

In the chemical composition each additional ingredient independently may differ from 2,2,4,4-tetrasilylpentasilane in function, composition, or structure; alternatively in function or composition; alternatively in function or structure; alternatively in composition or structure; alternatively in function; alternatively in composition; alternatively in structure. Function in this context means a chemical, physical, mechanical, or optical characteristic; alternatively chemical, physical, or mechanical; alternatively chemical or physical; alternatively chemical or mechanical; alternatively physical or mechanical; alternatively chemical; alternatively physical; alternatively mechanical. Composition means empirical formula, e.g., molecular formula. Structure means bonding arrangement of atoms and formal character of covalent bonds (single, double, triple, or aromatic bond) there between.

Each additional ingredient independently may be a covalently bonded substance, which independently may be a solid, liquid, or gas; alternatively a solid (e.g., one or more $Si_{80}$ precursors); alternatively a gas (e.g., monosilane and/or disilane dissolved in the 2,2,4,4-tetrasilylpentasilane); alternatively a liquid (e.g., trisilane, a tetrasilane, or a pentasilane such as neopentasilane). Each solid additional ingredient, when present, independently may be dissolved, alternatively suspended in the 2,2,4,4-tetrasilylpentasilane and, if unsuitable for characterization by GC, may be excluded or not counted in the area % (GC) concentration of the chemical composition. Each liquid additional ingredient, when present, independently may have a boiling point at 101.3 kPa of from 30° to 250° C., alternatively from 50° to 90° C., alternatively from 90° to 134° C., alternatively from 135° to 200° C. Each solid or liquid additional ingredient independently may comprise Si atoms, alternatively lack Si atoms.

In the chemical composition each additional ingredient independently may comprise C, H, and optionally one or more heteroatoms independently selected from N, O, and S, and optionally further comprise Si atoms, alternatively lack Si atoms. Each additional ingredient independently may be saturated, alternatively unsaturated, alternatively aromatic. At least one additional ingredient, alternatively each of two or more additional ingredients independently may be an additional precursor that is different than and useful with 2,2,4,4-tetrasilylpentasilane in the method of forming a silicon-containing material (e.g., film). The additional precursor may be a silicon-containing precursor other than 2,2,4,4-tetrasilylpentasilane (e.g., a different hydridosilane such as 2,2-disilyltrisilane or an organosilicon such as an organosilane such as trimethyl- or tetramethyl-monosilane, dichlorodimethyl-monosilane, or chlorotrimethyl-monosilane, or a silaalkane such as 1,3-disilabutane), alternatively an organic precursor lacking silicon (e.g., an alkane such as methane, including natural gas; carbon tetrachloride; propane; hexane; or a mixture of any two or more thereof), alternatively an inorganic precursor lacking silicon (e.g., anhydrous ammonia, molecular nitrogen, hydrazine, molecular oxygen, ozone, nitrous oxide, water, or hydrogen peroxide), alternatively a mixture thereof. Additionally or alternatively, the additional precursor may be a source of carbon comprising a carbon-containing precursor (e.g., the organosilicon), a source of oxygen comprising an oxygen-containing precursor (e.g., molecular oxygen, ozone, nitrous oxide, water, or hydrogen peroxide), or a source of nitrogen comprising nitrogen-containing precursor (e.g., anhydrous ammonia, molecular nitrogen, or hydrazine), or a combination of any two or more of the source of carbon comprising a carbon-containing precursor, the source of oxygen comprising an oxygen-containing precursor, and the source of nitrogen comprising nitrogen-containing precursor. The additional precursor may function as a solvent for the 2,2,4,4-tetrasilylpentasilane, or vice versa, in the chemical composition.

Alternatively or additionally, in the chemical composition the at least one additional ingredient may be a solvent or carrier gas for a precursor such as a solvent or carrier gas for the 2,2,4,4-tetrasilylpentasilane. The carrier gas may be a noble gas such as a gas of He or Ar. The solvent may be an organic solvent lacking Si or a structurally or compositionally different precursor such as a silicon-containing precursor other than the 2,2,4,4-tetrasilylpentasilane. The organic solvent may also function as a source of carbon-containing precursor, alternatively the source of carbon-containing precursor may also function as an organic solvent in the chemical composition.

Alternatively, the chemical composition consists essentially of 2,2,4,4-tetrasilylpentasilane, alternatively consists of 2,2,4,4-tetrasilylpentasilane. The chemical composition that consists essentially of 2,2,4,4-tetrasilylpentasilane lacks any other nonasilane isomer, alternatively lacks halosilanes, alternatively lacks any acyclic hydridosilanes having 10 or more Si atoms, alternatively lacks any cyclic hydridosilanes, alternatively lacks any cage-type hydridosilanes, alternatively lacks any other hydridosilanes, and organosilanes), alternatively lacks any other silane (including aminosilanes, halosilanes, hydridosilanes, and organosilanes), but otherwise may contain additional ingredients, e.g., an organic solvent, inert gas or a silicon-containing precursor other than the foregoing. The chemical composition that consists of 2,2,4,4-tetrasilylpentasilane lacks any other substance.

The chemical composition may further comprise 2,2-disilyltrisilane, wherein area % (GC) concentration of the 2,2,4,4-tetrasilylpentasilane is greater than the area % (GC) concentration of the 2,2-disilyltrisilane. The chemical composition may have a concentration of the 2,2,4,4-tetrasilylpentasilane that is at least 70 area % (GC) based on total GC area of the chemical composition. The chemical composition may be characterizable as having a total of from 0 to 9 area % (GC) of nonasilane structural isomers other than the 2,2,4,4-tetrasilylpentasilane. The chemical composition may be characterizable as lacking, i.e., has 0 area % (GC) (0 wt %) of nonasilane structural isomers other than the 2,2,4,4-tetrasilylpentasilane. Alternatively, the chemical composition may be characterizable as having a total of 0 area % (GC), alternatively from >0 to 9 area % (GC), alternatively from >0 to 8 area % (GC), alternatively from >0 to 7 area % (GC), alternatively from >0 to 6 area % (GC), alternatively from >0 to 5 area % (GC), alternatively from >0 to 4 area % (GC), alternatively from >0 to 3 area % (GC), alternatively from >0 to 2 area % (GC), alternatively from >0 to 1 area % (GC), alternatively from >0 to 0.5 area % (GC), of nonasilane structural isomers other than the 2,2,4,4-tetrasilylpentasilane. Alternatively, the chemical composition may be characterizable as having a total of 0 wt %, alternatively from >0 to 9 wt %, alternatively from >0 to 8 wt %, alternatively from >0 to 7 wt %, alternatively from >0 to 6 wt %, alternatively from >0 to 5 wt %, alternatively from >0 to 4 wt %, alternatively from >0 to 3 wt %, alternatively from >0 to 2 wt %, alternatively from >0 to 1 wt %, alternatively from >0 to 0.5 wt %, of nonasilane structural isomers other than the 2,2,4,4-tetrasilylpentasilane.

The method of making 2,2,4,4-tetrasilylpentasilane may be selective for making 2,2,4,4-tetrasilylpentasilane over other nonasilane structural isomers. The making step may be illustrated by the self-condensation reaction shown in the following reaction scheme:

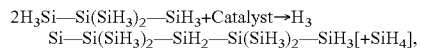
Si—Si(SiH$_3$)$_2$—SiH$_2$—Si(SiH$_3$)$_2$—SiH$_3$[+SiH$_4$], wherein Catalyst is the condensation reaction catalyst.

The 2,2-disilyltrisilane used in the method of making 2,2,4,4-tetrasilylpentasilane may be a purified form of 2,2-disilyltrisilane. The purified form of 2,2-disilyltrisilane may be a composition comprising at least 93 wt % of 2,2-disilyltrisilane; not greater than 5 wt % of other silanes; and not greater than 2 wt % of hydrocarbons; and a method of preparing the composition. The composition may comprise at least 97 wt % of 2,2-disilyltrisilane; alternatively at least 98 wt % of 2,2-disilyltrisilane; alternatively not greater than 3 wt % of other silanes; alternatively not greater than 1 wt % of hydrocarbons; alternatively at least 97 wt % of 2,2-disilyltrisilane, not greater than 3 wt % of other silanes, and not greater than 1 wt % of hydrocarbons. The 2,2-disilyltrisilane may be purified, and the immediately foregoing composition may be obtained, according to the purification method of U.S. Pat. No. 8,147,789 B2. In jurisdictions that allow incorporation by reference, we hereby incorporate by reference the subject matter of U.S. Pat. No. 8,147,789 B2 at column 2, line 33, to column 8, line 62. The method of making may be conducted in a reaction mixture consisting essentially of, alternatively consisting of the 2,2-disilyltrisilane, or the purified form thereof, and the condensation reaction catalyst. The reaction mixture consisting essentially of the 2,2-disilyltrisilane, or the purified form thereof, and the condensation reaction catalyst may contain an organic solvent.

The condensation reaction catalyst used in the method of making 2,2,4,4-tetrasilylpentasilane may be a silicate glass such as a borosilicate glass; a metal oxide such as sodium oxide, aluminum oxide, iron oxide, calcium oxide, magnesium oxide, potassium oxide, lead oxide, or barium oxide; an alloy of the silicate glass and one or more metal oxides, or a metal or metal alloy such as a stainless or carbon steel. In some embodiments the silicate glass is a silicate glass wool, alternatively a silicate glass wool lacking platinum. In some embodiments the condensation reaction catalyst may not be, and the method of making may not employ, glass wool; silica gel; platinum; glass wool-silica gel-platinum (5%); a lanthanide metal complex; or any of the glass wool, silica gel, platinum, and lanthanide metal complexes. The amount of the condensation reaction catalyst that is used in the method of making is a quantity sufficient for enhancing the self-condensation of 2,2-disilyltrisilane to give 2,2,4,4-tetrasilylpentasilane and, formally, monosilane as a by-product. When the condensation reaction catalyst is a borosilicate glass, the borosilicate glass may be in the form of a container (e.g., a flask) and the container may hold the 2,2-disilyltrisilane under suitable condensation reaction conditions for making the 2,2,4,4-tetrasilylpentasilane. The amount of the condensation reaction catalyst may be from 1 to 10,000 ppm, alternatively from 10 to 5,000 ppm, alternatively from 100 to 5,000 ppm, all based on the sum of the weight of the 2,2-disilyltrisilane plus the condensation reaction catalyst. The condensation reaction catalyst may be homogeneous or heterogeneous, alternatively homogeneous, alternatively heterogeneous.

The condensation reaction conditions suitable for use in the method of making 2,2,4,4-tetrasilylpentasilane comprise reaction temperature, pressure, reaction time period, reaction atmosphere, or any combination of two or more thereof. The reaction temperature may be from 0° to 200° C., alternatively from 20° C. to the boiling point of 2,2-disilyltrisilane (e.g., 134° C. at 101.3 kPa), alternatively from 30° to 100° C., alternatively from 18° to 30° C. The reaction pressure may be from 1 kPa to 1,000 kPa, alternatively from 50 kPa to 500 kPa, alternatively from 100 kPa to 200 kPa. The reaction time period may be from 1 hour to 100 days, although shorter and longer periods are contemplated in some embodiments. The reaction time period may be relatively longer at lower reaction temperatures and relatively shorter at higher reaction temperatures. Similarly, the reaction time period may be relatively longer with less active condensation reaction catalysts and relatively shorter with more active condensation reaction catalysts. For example, when the reaction temperature is from 100° to 134° C., the reaction time period may be from 1 to 24 hours. When the reaction temperature is from 18° to 30° C. and the condensation reaction catalyst is a borosilicate glass, the reaction time period may be from 1 day to 50 days. The condensation reaction conditions may further comprise an inert gas atmosphere such as a gas of N$_2$, He, or Ar. The condensation reaction conditions may further comprise, alternatively lack, agitating (e.g., stirring or shaking) the 2,2-disilyltrisilane and condensation reaction catalyst together.

The method of making 2,2,4,4-tetrasilylpentasilane may further comprise one or more additional steps before the making step, one or more additional steps after the making step, or a combination of one or more additional steps before and one or more additional steps after, the making step. The one or more additional steps are optional in the method of making. Examples of the one or more additional steps before the making step are purifying the 2,2-disilyltrisilane (e.g., according to the purification method of the U.S. Pat. No. 8,147,789 B2) to give the purified form of the 2,2-disilyltrisilane; contacting the 2,2-disilyltrisilane with the condensation reaction catalyst; or both purifying the 2,2-disilyltrisilane and contacting the resulting purified 2,2-disilyltrisilane with the condensation reaction catalyst. Examples of the one or more additional steps after the making step are purifying the 2,2,4,4-tetrasilylpentasilane (e.g., according to the present purifying method) to give a purified form of the 2,2,4,4-tetrasilylpentasilane and, optionally, a recovered portion of the 2,2-disilyltrisilane; separating the 2,2,4,4-tetrasilylpentasilane from the condensation reaction catalyst; recycling the recovered portion 2,2-disilyltrisilane back to a subsequent iteration of the method of making step (see below); or a combination of any two or more of the foregoing "after" additional steps.

In addition to 2,2,4,4-tetrasilylpentasilane, the product composition obtained from the method of making 2,2,4,4-tetrasilylpentasilane may further comprise monosilane, 2,2-disilyltrisilane (unreacted), or both monosilane and 2,2-disilyltrisilane.

In the method of purifying 2,2,4,4-tetrasilylpentasilane, the concentration of the 2,2,4,4-tetrasilylpentasilane in the remainder may be at least 70 area % (GC), alternatively at least 80 area % (GC), based on total GC area of the remainder. The separating may comprise evaporating, alternatively distilling, alternatively fractional distilling and the remainder may be an unevaporated remainder, undistilled remainder, or fractional undistilled remainder, respectively. The purifying method may further comprise distilling any unreacted 2,2-disilyltrisilane to give a recovered 2,2-disilyltrisilane, and contacting the recovered 2,2-disilyltrisilane with a condensation reaction catalyst under condensation reaction conditions so as to synthesize an additional quantity of the 2,2,4,4-tetrasilylpentasilane and make a product composition comprising the additional quantity of 2,2,4,4-tetrasilylpentasilane. The unreacted 2,2-disilyltrisilane being distilled may be 2,2-disilyltrisilane in the product composition that is produced by the method of making 2,2,4,4-tetrasilylpentasilane, alternatively 2,2-disilyltrisilane that has been separated from the remainder by the method of purifying 2,2,4,4-tetrasilylpentasilane, alternatively both.

In the method of purifying 2,2,4,4-tetrasilylpentasilane, the mixture comprising 2,2,4,4-tetrasilylpentasilane, monosilane, and 2,2-disilyltrisilane may be obtained from any source. For example, the mixture may be the product composition that is obtained from the method of making. Alternatively, the mixture may be obtained via a process that is different than the present method of making. The method of purifying may further comprise distilling the 2,2,4,4-tetrasilylpentasilane from the remainder to give a distillate comprising at least 90 area % (GC) 2,2,4,4-tetrasilylpentasilane.

In the method of forming a silicon-containing material, the method may initially form the silicon-containing film. The film typically is restricted in one dimension known as thickness. The film may have a thickness of from 0.1 nm to 10,000 nm, alternatively from 1 nm to 1,000 nm, alternatively from 1.0 nm to 200 nm. Continuing the method for a period of time sufficient to increase thickness of the silicon-containing film may give the silicon-containing material in a shape other than a film. Such other shape may be directed by a complimentary shape of the substrate. Such other shape may be geometrically irregular or regular. The regular geometric shape may be, e.g., a block, sphere, or ellipsoid. The material in such other shape may have a thickness of from >10 μm to 10,000 μm, alternatively a minimum dimension of from >10 μm to 10,000 μm.

In the method of forming a silicon-containing material (e.g., film) the first and second substrates independently may comprise an electrically conductive or insulating and/or a thermally conductive or insulating material. The first and second substrates independently may be the same or different material such as a semiconductor material such as monocrystalline or polycrystalline silicon. The seed layer may comprise silicon grains disposed on and in contact with the surface of the second substrate, and the method may comprise forming the silicon-containing material (e.g., film) on and in contact with the seed layer. The precursor composition may comprise at least 70 area % (GC), alternatively at least 80 area % (GC) of 2,2,4,4-tetrasilylpentasilane based on total GC area of the precursor composition. The precursor composition comprising 2,2,4,4-tetrasilylpentasilane may be the chemical composition, alternatively neat 2,2,4,4-tetrasilylpentasilane. That is, the concentration of the 2,2,4,4-tetrasilylpentasilane in the precursor composition comprising 2,2,4,4-tetrasilylpentasilane may be 100 area % (GC), alternatively <100 area % (GC), alternatively <99 area % (GC).

In the method of forming a silicon-containing material (e.g., film) one or more silicon-containing precursors may be used to prepare the silicon-containing material (e.g., film) according to the material (e.g., film)-forming deposition method. At least one of the silicon-containing precursors is the 2,2,4,4-tetrasilylpentasilane. When two or more precursors are used, the 2,2,4,4-tetrasilylpentasilane may be used in admixture with the other silicon-containing precursors, alternatively at least one of the other silicon-containing precursors may be used to form a seed layer, and then the 2,2,4,4-tetrasilylpentasilane may be used to form the silicon-containing material (e.g., film) on and in direct contact with the seed layer.

In the method of forming a silicon-containing material (e.g., film), the material (e.g., film) deposition method may comprise a vapor deposition method or a solution deposition method. The material (e.g., film) deposition method may be a chemical vapor deposition method, alternatively a plasma enhanced chemical vapor deposition method or a thermal chemical vapor deposition method. Examples of vapor deposition methods useful in the present invention are CVD, PVD, and ALD. The CVD methods may be categorized broadly as thermal or heat based or plasma enhanced. Examples of types of CVD methods that are useful include APCVD (pressure 95 to 105 kilopascals), LPCVD (pressure 0.001 pascals (Pa.)<pressure<10 Pa.), UHVCVD (pressure<1×10$^{-6}$ pascals), PECVD, ALCVD, CCVD (thermal based), HWCVD (thermal based), HPCVD, RTCVD (thermal based), VPE (thermal based), and PICVD. Solution deposition involves polymerization of a volatile precursor from solution onto a substrate or deposition of a nonvolatile polymer from solution onto a substrate. Examples of solution deposition methods useful in the present invention are spray coating, dip coating, printing, and SOD. The solution deposition method may be spray coating or SOD, alternatively spray coating, alternatively dip coating, alternatively printing, alternatively SOD.

The silicon-containing material (e.g., film) formed by the method of forming thereof may be an elemental silicon material (e.g., film), a silicon carbide material (e.g., film), a silicon oxide material (e.g., film), a silicon nitride material (e.g., film), a silicon carbonitride material (e.g., film), or a silicon oxycarbonitride material (e.g., film). The material (e.g., film) deposition method for forming the silicon carbide material (e.g., film), silicon oxide material (e.g., film), silicon nitride material (e.g., film), silicon carbonitride material (e.g., film), or silicon oxycarbonitride material (e.g., film) further comprises contacting the exposed surface of the first substrate, or the seed layer disposed on the surface of the second substrate, respectively with the additional precursor such as a source of carbon comprising a carbon-containing precursor, a source of oxygen comprising an oxygen-containing precursor (e.g., molecular oxygen, ozone, nitrous oxide, water, or hydrogen peroxide), or a source of nitrogen comprising nitrogen-containing precursor (e.g., anhydrous ammonia, molecular nitrogen, or hydrazine), or a combination of any two or more of the source of carbon comprising a carbon-containing precursor, the source of oxygen comprising an oxygen-containing precursor, and the source of nitrogen comprising nitrogen-containing precursor. The contacting step prepares the material (e.g., film).

The method of forming the silicon carbide material (e.g., film), silicon oxide material (e.g., film), silicon nitride material (e.g., film), silicon carbonitride material (e.g., film), or silicon oxycarbonitride material (e.g., film) employs the 2,2,4,4-tetrasilylpentasilane and one or more of the ad rem additional precursor(s) with the intended non-Si element(s) (e.g., C; O; N; C and N; or O, C and N, respectively). The combination of any two or more of the additional precursors is chosen to provide the ad rem material (e.g., film) with the intended non-Si element(s). The combination may comprise (a) a mixture of two or more different additional precursors, each containing a different one of C, O, and N; (b) a single precursor comprising two or more of the C, N, and O atoms; or both (a) and (b). For example, the silicon carbide material (e.g., film) may be prepared from a precursor combination comprising the 2,2,4,4-tetrasilylpentasilane and a mixture of the carbon-containing precursor lacking N and O. The carbon-containing precursor lacking N and O and useful for preparing the silicon carbide material (e.g., film) may be trimethyl- or tetramethyl-monosilane, dichlorodimethyl-monosilane, or chlorotrimethyl-monosilane, or a silaalkane such as 1,3-disilabutane. The silicon carbonitride material (e.g., film) may be prepared from a precursor combination comprising the 2,2,4,4-tetrasilylpentasilane and a mixture of the carbon-containing and nitrogen-containing precursor(s), which is a collection of molecules containing both C and N and lacking O or are different molecules in that one additional precursor contains C but not N or O and the other additional precursor contains N but not C or O. The carbon-and-nitrogen-containing precursor useful for preparing the silicon carbonitride material (e.g., film) may be alkylaminosilane such as tris(dimethylamino)silane and the carbon-containing and nitrogen-containing precursors may be a mixture of different molecules such as a mixture of trimethyl or tetramethyl-monosilane and ammonia. Alternatively, the silicon carbonitride material (e.g., film) may be prepared from a precursor combination comprising the 2,2,4,4-tetrasilylpentasilane and a carbon-and-nitrogen-containing precursor or a collection of such precursors wherein each such precursor contains C and N. The silicon oxycarbonitride material (e.g., film) may be prepared from a precursor combination comprising the 2,2,4,4-tetrasilylpentasilane and (a) a mixture the carbon-containing precursor and an oxygen-containing precursor such as molecular oxygen or (b) a carbon-and-oxygen-containing precursor such as an organosiloxane such as hexamethyldisiloxane or a cyclic organosiloxane such as tetrakis(dimethylsiloxane) (D4). The elemental silicon material (e.g., film) consists essentially of Si atoms and may be amorphous, polycrystalline, or epitaxial.

A compound that is 2,2,4,4,6,6-hexasilylheptasilane may be used as a silicon-containing precursor as the 2,2,4,4-tetrasilylpentasilane described above. For example, the silicon-containing precursor may be used to form silicon-containing materials, such as crystalline silicon and other silicon-containing materials. The 2,2,4,4,6,6-hexasilylheptasilane may be formed by condensing neopentasilane and 2,2,4,4-tetrasilylpentasilane in the presence of a catalyst, similar to the condensation reaction used in forming 2,2,4,4-tetrasilylpentasilane from neopentasilane described herein.

The invention is further illustrated by, and an invention embodiment may include any combinations of features and limitations of, the non-limiting examples thereof that follow.

GC conditions: a capillary column with 30 meters length, 0.32 mm inner diameter, and containing a 0.25 μm thick stationary phase in the form of a coating on the inner surface of the capillary column, wherein the stationary phase was composed of phenyl methyl siloxane. Carrier gas was helium gas used at a flow rate of 105 mm per minute. GC instrument was an Agilent model 7890A gas chromatograph. Inlet temperature was 150° C. GC experiment temperature profile consisted of soaking (holding) at 50° C. for 2 minutes, ramping temperature up at a rate of 15° C./minute to 250° C., and then soaking (holding) at 250° C. for 10 minutes.

Ex. 1: synthesis of 2,2,4,4-tetrasilylpentasilane: Allowed 110.0 g of 2,2-disilyltrisilane with 98.4 wt % purity to stand in a freshly cleaned borosilicate glass flask where the surface was not passivated at room temperature (25° C.) for 42 days. Distilled the resulting product composition at up to 125° C. under full vacuum to remove more volatile ingredients, including unreacted 2,2-disilyltrisilane. The undistilled remainder was recovered as a clear liquid; yield 11.3 g (11.5%). The undistilled remainder was found to contain 82 area % (GC) of 2,2,4,4-tetrasilylpentasilane. Consistent with 2,2,4,4-tetrasilylpentasilane are analytical data. $^1$H-NMR: ($C_6D_6$) 3.55 ppm (singlet, $SiH_3$), 3.67 ppm (singlet, $SiH_2$); $^{29}$Si-NMR: (δ)-156.7 ppm (quaternary Si) and HSQC NMR spectroscopy and HMBC NMR spectroscopy analyses were consistent with 2,2,4,4-tetrasilylpentasilane. GC-MS (sample dissolved in $C_6D_6$); fragments were consistent with 2,2,4,4-tetrasilylpentasilane.

Ex. 2: thermal properties of 2,2,4,4-tetrasilylpentasilane: 2,2,4,4-tetrasilylpentasilane was found to be non-pyrophoric at the ambient temperature (25° C.) and start thermal decomposition at 273° C. by DSC using instrument Mettler Toledo TGA/DSC and temperature profile 35° to 400° C. at a ramp rate of 10° C. per minute. The 2,2,4,4-tetrasilylpentasilane was found to have a boiling point at approximately 230° C. by GC. Thus, 2,2,4,4-tetrasilylpentasilane has sufficient vapor pressure for use in vapor deposition type material (e.g., film) forming deposition methods, including PECVD and thermal based CVD methods, including thermal based LPCVD methods at low temperature (e.g., from 200° to 600° C., alternatively from 300° to <600° C., alternatively from 200° to <500° C.).

Ex. 3 (prophetic): forming a silicon film using 2,2,4,4-tetrasilylpentasilane with LPCVD: using a LPCVD reactor and a bubbler containing 2,2,4,4-tetrasilylpentasilane and in fluid communication with the LPCVD reactor, heat the bubbler containing 2,2,4,4-tetrasilylpentasilane to 70° C. to increase vapor pressure thereof. Then flow He carrier gas through the bubbler to carry vapor of 2,2,4,4-tetrasilylpentasilane into the LPCVD reactor, wherein the LPCVD reactor contains a plurality of vertically oriented and spaced apart silicon wafers heated to 500° C. so a conformal elemental silicon film is formed on the wafers.

Ex. 4 (prophetic): forming a silicon nitride film using 2,2,4,4-tetrasilylpentasilane with PECVD: using a PECVD reactor and a bubbler in fluid communication with the PECVD reactor, heat the bubbler containing 2,2,4,4-tetrasilylpentasilane to 70° C. to increase vapor pressure thereof. Then flow He carrier gas through the bubbler to carry vapor of 2,2,4,4-tetrasilylpentasilane into the PECVD reactor, wherein the PECVD reactor has an ammonia-derived plasma and contains a plurality of horizontally oriented and spaced apart silicon wafers heated to 500° C. such that a conformal silicon nitride film is formed on the wafers.

Ex. 5: forming a silicon oxide film using 2,2,4,4-tetrasilylpentasilane with spray coating: applied a 5 wt % solution of 2,2,4,4-tetrasilylpentasilane in benzene to a silicate glass dish (a first substrate) in air, allowed the benzene to evaporate so as to form a liquid coating of 2,2,4,4-tetrasilylpentasilane on the dish, and allowed the 2,2,4,4-tetrasilylpentasilane to air oxidize over 30 minutes at 25° C. such that a conformal silicon oxide film was formed on the dish.

Ex. 6 (prophetic): forming an elemental silicon film using 2,2,4,4-tetrasilylpentasilane with spray coating: apply a 5 wt % solution of 2,2,4,4-tetrasilylpentasilane in toluene to a silicate glass dish (a first substrate) under helium atmosphere, allow the toluene to evaporate so as to form a liquid coating of 2,2,4,4-tetrasilylpentasilane on the dish, and heat the 2,2,4,4-tetrasilylpentasilane to 150° C., then to 500° C. under helium such that a conformal elemental silicon film is formed on the dish.

Ex. 7 (prophetic): forming a silicon film using 2,2,4,4-tetrasilylpentasilane on a seed layer with LPCVD: use a LPCVD reactor, a bubbler containing alkylaminosilane, and a bubbler containing 2,2,4,4-tetrasilylpentasilane, wherein each bubbler is independently in fluid communication with the LPCVD reactor. Heat the bubbler containing alkylaminosilane to 70° C. to increase vapor pressure thereof. Then flow He carrier gas through the bubbler to carry vapor of the alkylaminosilane into the LPCVD reactor, wherein the LPCVD reactor contains a plurality of vertically oriented and spaced apart silicon wafers (second substrates) heated to 500° C. such that a seed layer of silicon grains is formed on the wafers. Disconnect the alkylaminosilane bubbler. Purge the LPCVD reactor with He gas to remove residual alkylaminosilane therefrom. Heat the bubbler containing 2,2,4,4-tetrasilylpentasilane to 70° C. to increase vapor pressure thereof. Then flow He carrier gas through the bubbler to carry vapor of 2,2,4,4-tetrasilylpentasilane into the LPCVD reactor such that a conformal elemental silicon film is formed on the seed layer of silicon grains disposed on the wafers.

Ex. 8a to 8e (prophetic): replicate Ex. 3 to 7, respectively, except continue the deposition method until a silicon-containing material is formed having a thickness of 10 mm.

Ex. 9. Synthesis of 2,2,4,4-Tetrasilylpentasilane. To a 100 ml freshly cleaned borosilicate glass flask where the surface was not passivated was loaded 2.0 ml NPS with 98+% purity. The flask was heated in a heating mantle at 100° C. for 24 hours. The composition of the liquid content was analyzed with GC-MS. The integrations of GC-MS signals were previously calibrated with $^1$H NMR to be quantitative. 2,2,4,4-Tetrasilylpentasilane was formed almost exclusively at 30% conversion. Compared to the 9.4% conversion in Example 1, the conversion was improved by 3.2 times.

In some embodiments, the invention excludes any one of Ex. 1 to 9, alternatively any one of Ex. 3 to 8a and 9, alternatively any one of Ex. 3, 4, 6, 7, 8a to 8e, and 9.

The below claims are incorporated by reference here, and the terms "claim" and "claims" are replaced by the term "aspect" or "aspects," respectively. Embodiments of the invention also include these resulting numbered aspects.

What is claimed is:

1. A method of making 2,2,4,4-tetrasilylpentasilane, the method comprising contacting 2,2-disilyltrisilane with a condensation reaction catalyst under condensation reaction conditions so as to synthesize the 2,2,4,4-tetrasilylpentasilane and make a product composition comprising the 2,2,4,4-tetrasilylpentasilane.

2. The method of claim 1, wherein the product composition further comprises monosilane and 2,2-disilyltrisilane.

3. A method of purifying a mixture comprising 2,2,4,4-tetrasilylpentasilane, monosilane, and 2,2-disilyltrisilane, the method comprising separating the monosilane and 2,2-disilyltrisilane from the 2,2,4,4-tetrasilylpentasilane to give a remainder comprising 2,2,4,4-tetrasilylpentasilane and lacking the separated monosilane and 2,2-disilyltrisilane, wherein concentration of the 2,2,4,4-tetrasilylpentasilane in the remainder is greater than concentration of the 2,2,4,4-tetrasilylpentasilane in the mixture.

4. The method of claim 3, wherein concentration of the 2,2,4,4-tetrasilylpentasilane in the remainder is at least 70 area percent (area %, gas chromatograph (GC)) based on total GC area of the remainder.

5. The method of claim 3 further comprising distilling the 2,2,4,4-tetrasilylpentasilane from the remainder to give a distillate comprising at least 90 area % 2,2,4,4-tetrasilylpentasilane.

6. The method of claim 3 further comprising distilling any unreacted 2,2-disilyltrisilane to give a recovered 2,2-disilyltrisilane, and contacting the recovered 2,2-disilyltrisilane with a condensation reaction catalyst under condensation reaction conditions so as to synthesize an additional quantity of 2,2,4,4-tetrasilylpentasilane and make a product composition comprising the additional quantity of 2,2,4,4-tetrasilylpentasilane.

7. A method of forming a silicon-containing material on and in contact with a surface of a first substrate or on and in contact with a seed layer disposed on a second substrate, the method comprises contacting an exposed surface of a first substrate lacking a seed layer or contacting a seed layer disposed on a surface of a second substrate, to vapor of a precursor composition comprising 2,2,4,4-tetrasilylpentasilane, wherein the contacting comprises a material deposition method and forms a silicon-containing material on and in contact with the exposed surface of the first substrate or on and in contact with the seed layer disposed on the surface of the second substrate.

8. The method of claim 7 comprising a method of forming a silicon-containing film on and in contact with a surface of a first substrate or on and in contact with a seed layer disposed on a second substrate, the method comprises contacting an exposed surface of a first substrate lacking a seed layer or contacting a seed layer disposed on a surface of a second substrate, to vapor of a precursor composition comprising 2,2,4,4-tetrasilylpentasilane, wherein the contacting comprises a film deposition method and forms a silicon-containing film on and in contact with the exposed surface of the first substrate or on and in contact with the seed layer disposed on the surface of the second substrate.

9. The method of claim 8, wherein the method comprises forming the silicon-containing film on and in contact with the seed layer disposed on the surface of the second substrate.

10. The method of claim 8, (a) wherein the precursor composition comprises at least 70 area percent (area %, gas chromatograph (GC)) of 2,2,4,4-tetrasilylpentasilane based on total GC area of the precursor composition; (b) wherein the film deposition method is a chemical vapor deposition method or a solution deposition method; or (c) both (a) and (b).

11. The method of claim 10, wherein the film deposition method is the chemical vapor deposition method, which is a plasma enhanced chemical vapor deposition method or a thermal chemical vapor deposition method.

12. The method of claim 8, wherein the silicon-containing film is an elemental silicon film, a silicon carbide film, a silicon oxide film, a silicon nitride film, a silicon carbonitride film, or a silicon oxycarbonitride film; wherein the film deposition method for forming the silicon carbide film, silicon oxide film, silicon nitride film, silicon carbonitride film, or silicon oxycarbonitride film further comprises contacting the exposed surface of the first substrate, or the seed layer disposed on the surface of the second substrate, respectively with a source of carbon comprising a carbon-containing precursor, a source of oxygen comprising an oxygen-containing precursor, a source of nitrogen comprising nitrogen-containing precursor, or a combination of any two or more of the source of carbon comprising a carbon-containing precursor, the source of oxygen comprising an oxygen-containing precursor, and the source of nitrogen comprising nitrogen-containing precursor.

* * * * *